United States Patent
Plank et al.

(10) Patent No.: US 6,745,916 B2
(45) Date of Patent: Jun. 8, 2004

(54) UNIT AND METHOD FOR AUTOMATIC DELIVERY OF SPECIMEN SLIDES TO A COVERSLIPPER

(75) Inventors: Heinz Plank, Wr. Neudorf (AT); Hubert Goll, St. Poelten (AT); Siegfried Tanki, Stegersbach (AT)

(73) Assignee: Leica Mikrosysteme GmbH, Vienna (AT)

( * ) Notice: Subject to any disclaimer, the term of this patent is extended or adjusted under 35 U.S.C. 154(b) by 94 days.

(21) Appl. No.: 10/233,735

(22) Filed: Sep. 3, 2002

(65) Prior Publication Data

US 2003/0047567 A1 Mar. 13, 2003

(30) Foreign Application Priority Data

Sep. 7, 2001 (DE) .......................................... 101 44 041

(51) Int. Cl.⁷ .............................................. B65G 59/00
(52) U.S. Cl. ............................................. 221/1; 436/46
(58) Field of Search .............................. 221/1, 197, 92; 414/267; 436/174, 46, 43; 422/63, 65

(56) References Cited

U.S. PATENT DOCUMENTS

2003/0049172 A1 * 3/2003 Thiem ......................... 422/65

2004/0002163 A1 * 1/2004 Reinhardt et al. ........... 436/174

FOREIGN PATENT DOCUMENTS

DE 295 14 506 U1 12/1995

OTHER PUBLICATIONS

LEICA CV 5000—The new robotic coverslipper for histology and cytology laboratories, Leica Instruments GmbH, Nussloch, Germany, Dec., 1995.

* cited by examiner

*Primary Examiner*—Kenneth W. Noland
(74) *Attorney, Agent, or Firm*—Hodgson Russ LLP

(57) ABSTRACT

The invention concerns a unit (2) for automatic delivery of specimen slides to a coverslipper (3). The unit (2) comprises a housing (27) in which a front panel (25) is provided. Also provided is a passage (20) in the housing (27) that is defined substantially by a first and a second cutout (21 and 23) in the first and the second side wall (22 and 24). A transfer position (8) for racks (4) is provided in the region of the cutout (21) in the first side wall (22), and a transport apparatus (9) extends out substantially from the transfer position (8) to beyond the cutout (23) in the second side wall (24).

13 Claims, 7 Drawing Sheets

UNIT AND METHOD FOR AUTOMATIC DELIVERY OF SPECIMEN SLIDES TO A COVERSLIPPER

CROSS REFERENCE TO RELATED APPLICATIONS

This application claims priority of the German patent application 101 44 041.3 filed Sep. 7, 2001 which is incorporated by reference herein.

FIELD OF THE INVENTION

The invention concerns a unit for automatic delivery of specimen slides to a coverslipper. The invention further concerns a method for automatic delivery of specimen slides to a coverslipper.

BACKGROUND OF THE INVENTION

An automatic stainer and coverslipper are two separate units. According to the existing art, after the staining operation the specimen slides need to be manually removed from the stainer and inserted into the coverslipper in order to start the process of covering them with coverslips (see Leica brochure CV 5000). Despite the automation of the individual units, manual loading of the coverslipper is necessary. Smooth operation requires that laboratory personnel occupy themselves, at very short intervals of a few minutes, with removing racks from the stainer and loading the coverslipper.

German Utility Model DE 295 14 506 discloses a specimen slide coverslipper. The specimen slides are located in a magazine device with which they can be introduced into the coverslipper. There a covering medium is applied onto the specimen slides, and a transport device is used to remove a coverslip from a magazine and place it onto the specimen slide. The subject matter of the Utility Model is not capable, however, of proposing an automatic solution with which the specimen slides can be transferred into the coverslipper.

SUMMARY OF THE INVENTION

It is the object of the invention to create a unit with which specimen slides are delivered from a stainer to a coverslipper with no demands on an operator. The intention is also to ensure delivery in the most automatic, effective, and malfunction-free fashion possible.

This object is achieved by means of a unit comprising a housing including a bottom, a front panel, a back wall opposite the front panel, and first and second side walls opposite one another, wherein the housing has a passage therethrough defined by respective cutouts in the first and the second side walls; a transfer position for a rack of specimen slides provided near the cutout in the first side wall; and a transport apparatus extending out from the transfer position to beyond the cutout in the second side wall.

A further object of the invention is to create a method with which specimen slides are delivered from a stainer to a coverslipper with no demands on an operator. The delivery is intended to be as automated as possible, and efficient to a high degree.

The above object is achieved by means of a method that comprises the steps of depositing a rack with specimen slides in a transfer position of a unit for delivering specimen slides to the coverslipper; picking up the rack from the transfer position using a transport apparatus; displacing the rack in the unit toward the coverslipper; and lowering the rack with the specimen slides into the coverslipper.

It has proven particularly advantageous that the unit comprises a housing which also possesses a front panel. By opening the front panel the user can, for example, remove the empty racks and those temporarily stored in the unit. The unit itself comprises a passage that is defined substantially by a first and a second cutout in the first and the second side walls of the unit. The unit defines a transfer position for racks in the region of the cutout in the first side wall, and a transport apparatus extends out substantially from the transfer position to beyond the cutout in the second side wall. The unit is arranged between the stainer and the coverslipper. From the stainer, a rack with specimen slides is transferred to the transfer position in the unit. The transfer is accomplished with a transport arm, movable in two axes, in the stainer. The transport apparatus that is connected to the unit effects transport of the rack from the transfer position into the coverslipper or from the coverslipper into the storage position. The transport apparatus is substantially parallel to the back wall of the unit.

The transport apparatus comprises a rail, parallel to the back wall of the unit, on which a gripper for the racks is displaceable perpendicular to and parallel to the rail.

In the unit itself, a storage position for empty racks, i.e. racks without specimen slides, is provided between the first and the second side wall. The storage position can be configured as a chute that is arranged at an inclination with respect to the bottom of the unit in such a way that the racks without specimen slides slide toward the front panel.

The method for automatic delivery of specimen slides to a coverslipper is advantageously characterized in that a rack with specimen slides is deposited in a transfer position of a unit for delivering specimen slides to the coverslipper. The racks are then picked up from the transfer position by a transport apparatus. The rack is displaced in the unit toward the coverslipper by means of the transport apparatus, and the rack is lowered into the coverslipper.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
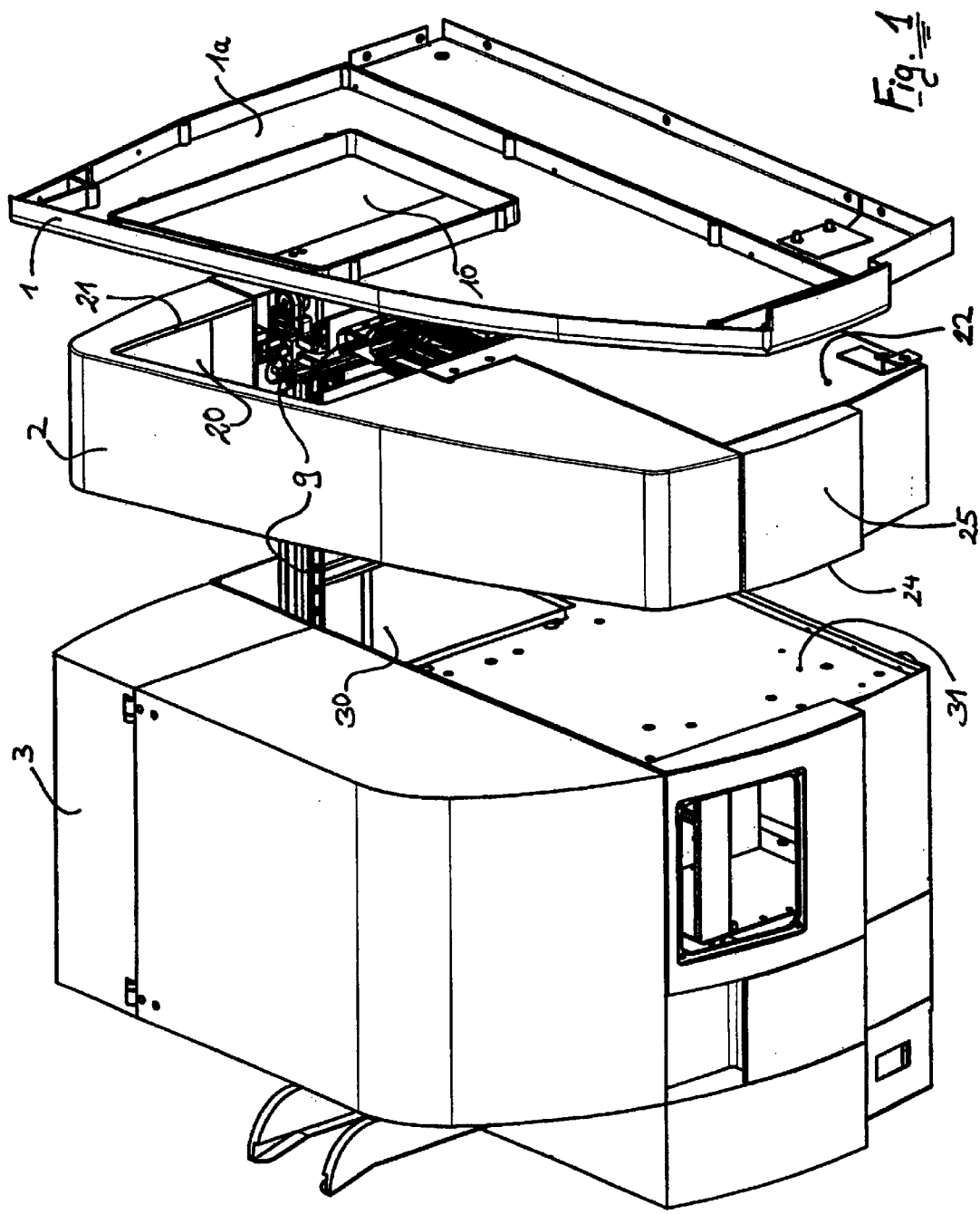
FIG. 1 schematically depicts the system made up of a stainer, a loading station, and a coverslipper.

FIG. 1 schematically depicts the system made up of a stainer 1, a unit (loading station) 2, and a coverslipper 3. In the depiction of FIG. 1, stainer 1, unit 2, and coverslipper 3 are shown separated from one another for better clarity. In the depiction selected for FIG. 1, only one side wall 1a of stainer 1 is depicted (see German Patent Application DE 100 41 229.7 for a complete description of the stainer). In operation, stainer 1, unit 2, and coverslipper 3 are connected to one another. It is evident from FIG. 1 that stainer 1 (German Patent Application DE 100 41 229.7) comprises at least one lateral opening 10 through which a transport apparatus 9 can pass. Specifically, transport apparatus 9 is used on the one hand to accept racks with specimen slides from other devices and to transfer racks with specimen slides for transfer to unit 2. Unit 2 is provided between stainer 1 and coverslipper 3, and thus connects stainer 1 to coverslipper 3. Stainer 1 places the rack with the stained specimen slides onto a transfer position (see FIG. 2); for that purpose, unit 2 has a passage 20 that is defined by a cutout 21 in first side wall 22 and a cutout 23 in second side wall 24. Unit 2 possesses a front panel 25 through which access to the interior of unit 2 is possible. Unit 2 is followed by coverslipper 3. An opening 30, through which unit 2 can transfer racks with specimen slides into coverslipper 3 and can remove racks without specimen slides from coverslipper 3, is also provided in a side wall 31 of coverslipper 3 opposite second side wall 24 of unit 2. Communication between coverslipper 3 and stainer 1 occurs as follows: stainer 1 queries whether it can place a rack in coverslipper 3. The response from coverslipper 3 can be "yes" or "no." If "no," the query is repeated at periodic intervals. If "yes," the rack is put in place and a "rack transferred" message is generated. Coverslipper 3 responds "rack received." This procedure eliminates long waiting times for the rack in the transfer position. A quick transfer is advantageous because the specimen slides usually sit in a bath of solvent (often xylene), and wet specimen slides that were just recently stored in solvent exhibit considerably better flow behavior for the coverslip adhesive.

Figure 2:
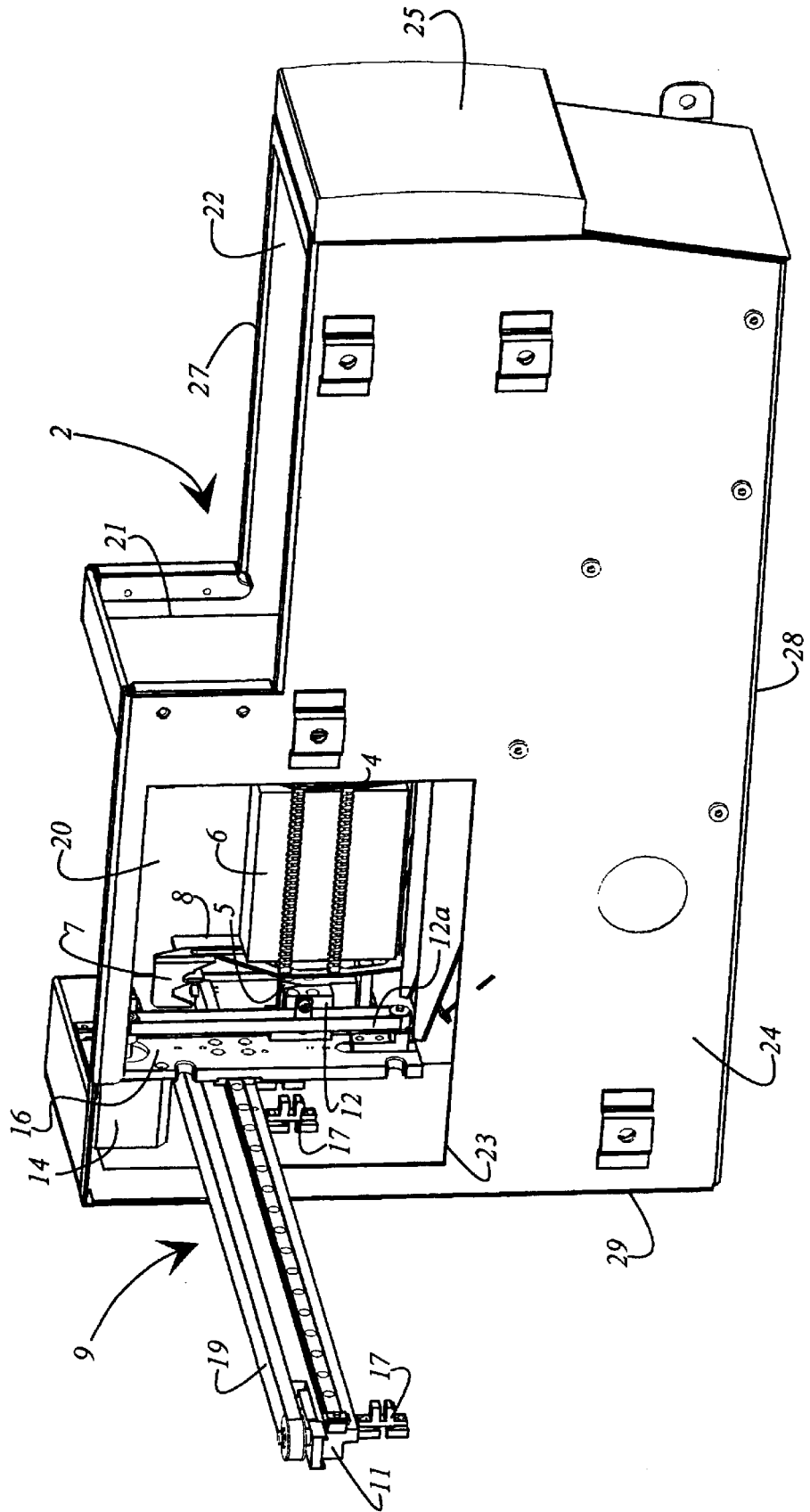
FIG. 2 is a perspective depiction of the loading station, a rack with specimen slides coming from the stainer being parked in the transfer position of the loading station.

FIG. 2 depicts unit 2 in perspective, a rack 4 with specimen slides 6 coming from stainer 1 being parked in a transfer position 8 of unit 2. Parking in transfer position 8 does not occur until stainer 1 has received a "yes" from coverslipper 3 for that purpose. Stainer 1 sends to unit 2, via the interface (not depicted), a command that handling of rack 4 can begin. Unit 2 comprises a transport apparatus 9 that projects through opening 30 into coverslipper 3. Rack 4 is retrieved by transport apparatus 9 at transfer position 8, and transported into coverslipper 3. In addition, after coverslipping, empty racks 4 can also be retrieved by the same transport apparatus 9 from coverslipper 3. Unit 2 comprises a housing 27 that has a bottom 28, a front panel 25, a back wall 29 opposite front panel 25, and a first and second side wall 22 and 24 opposite one another. Also configured in unit 2 is a passage 20 that is substantially defined by a first and a second cutout 21 and 23 in first and second side walls 22 and 24. Transfer position 8 for racks 4 is provided in the region of first cutout 21 in first side wall 22. Transport apparatus 9 is constructed from a rail 11, parallel to back wall 29 of unit 2, on which a gripper 12 for racks 4 is displaceable perpendicular to and parallel to rail 11. Gripper 12 is connected to a belt 12a that can be driven via a first motor 14. The running direction of belt 12a is perpendicular to rail 11. Gripper 12, belt 12a, and first motor 14 are carried by a baseplate 16. Baseplate 16 is movable along rail 11 by way of a belt 19 driven by a second motor 18 (see FIG. 4). Also provided along rail 11 are several light barriers 17 which serve to monitor and control the position of baseplate 16, providing information about the working status of unit 2.

Rack 4 possesses at least one structured angled piece 7 that is used to transport rack 4. As already mentioned above, gripper 12 is displaceable perpendicular to rail 11. Gripper 12 comprises a groove 5 that snaps into an angled piece 7 of rack 4. Rack 4 is thus retained on only one side.

Figure 3:
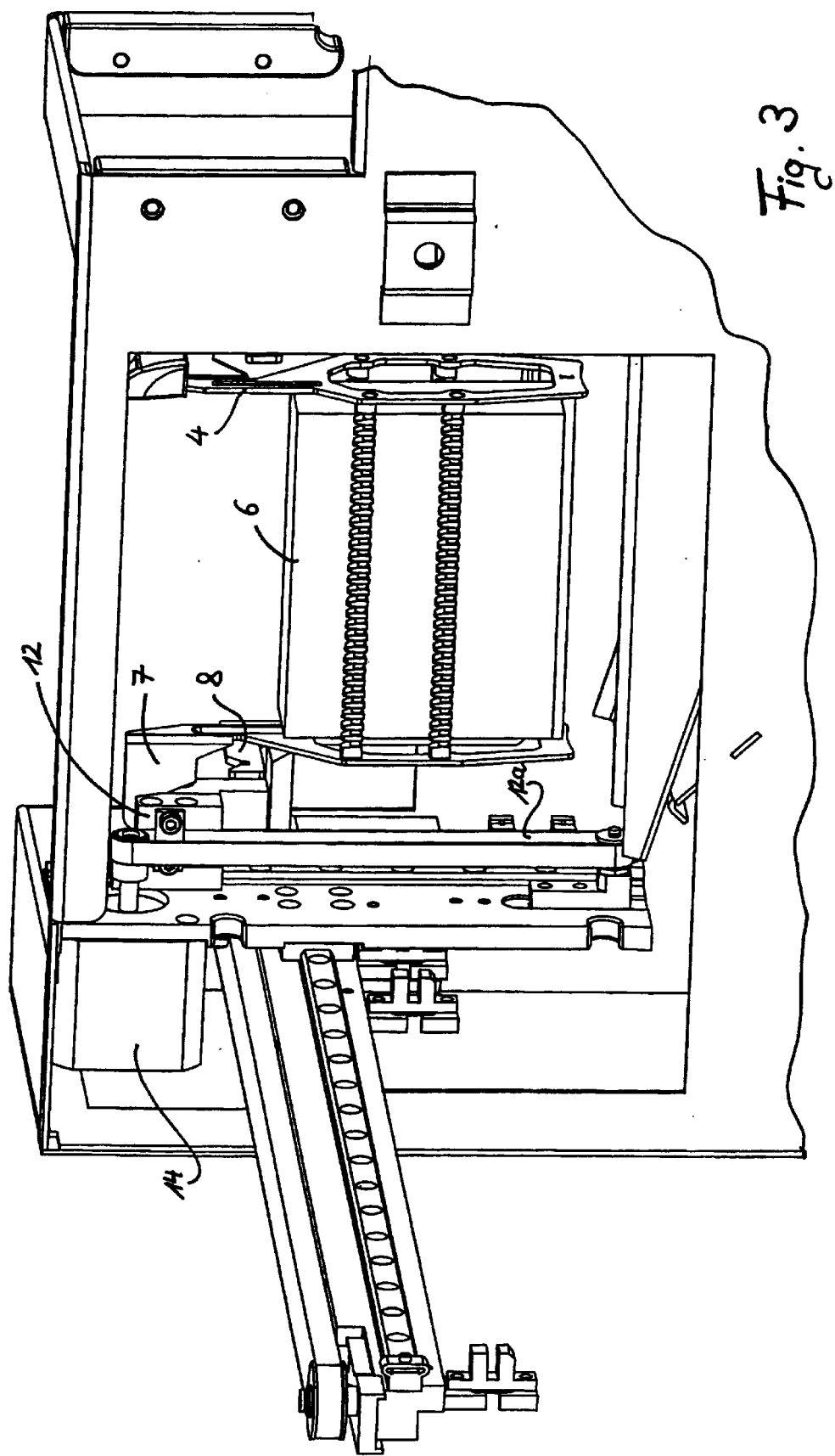
FIG. 3 is a perspective depiction of the loading station, the rack having been lifted from the transfer position and parts having been omitted for clarity.

In FIG. 3, gripper 12 has been moved by first motor 14, by way of belt 12a, in order to come into engagement with angled piece 7 of rack 4. Rack 4 is thereby lifted up, together with specimen slides 6, from transfer position 8.

Figure 4:
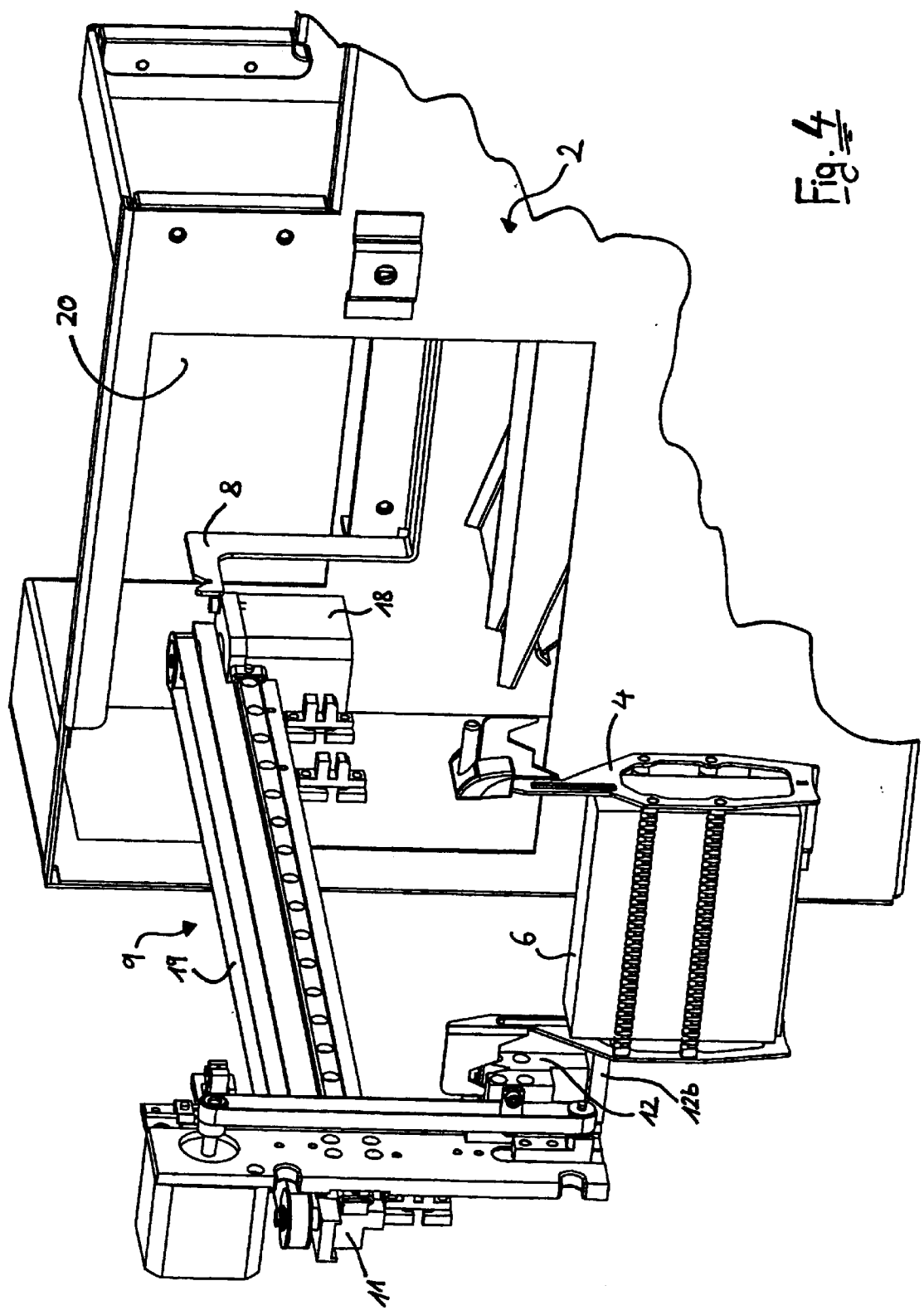
FIG. 4 is a perspective depiction of the loading station, the rack having been shifted toward the coverslipper and parts having been omitted for clarity.

Then, as depicted in FIG. 4, second motor 18 is energized and rack 4, retained on gripper 12, is displaced with specimen slides 6 along rail 11. The rotary motion of second motor 18 is converted by a belt 19 into the translational motion along rail 11. Provided on gripper 12 is a support element 12b that holds the rack in a stable horizontal position. Rack 4 is displaced by transport apparatus 9 sufficiently far out of passage 20 of unit 2 that rack 4, together with specimen slides 6, can be lowered into coverslipper 3. Transport apparatus 9 transports rack 4 through lateral opening 30 into coverslipper 3. There rack 4, together with specimen slides 6, is lowered into a tank (not depicted) of solvent. Coverslipper 3 detects rack 4, and the coverslipping operation is started. Once all the specimen slides have been coverslipped and deposited into separate output racks (not depicted) in the coverslipper, the empty rack 4 is transported away.

Figure 5:
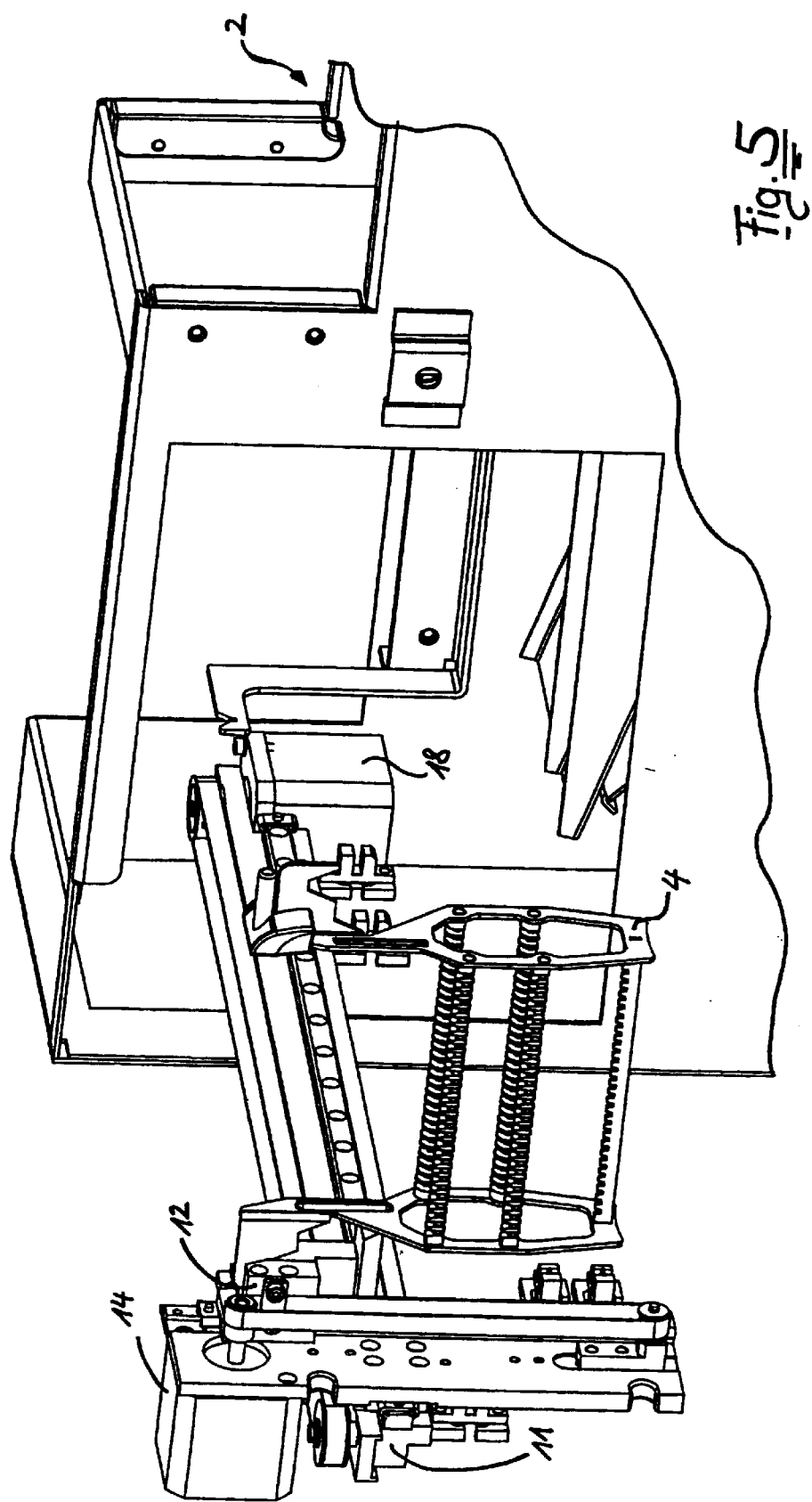
FIG. 5 is a perspective depiction of the loading station, an empty rack having been removed from the coverslipper and parts having been omitted for clarity.

For that purpose, as depicted in FIG. 5, the empty rack 4 is removed from the coverslipper by means of gripper 12. Firstly, first motor 14 is operated in order to raise rack 4 in coverslipper 3 to the height of opening 30. Once that has been done, second motor 18 is operated, and the empty rack 4 is transported back along rail 11 into unit 2.

Figure 6:
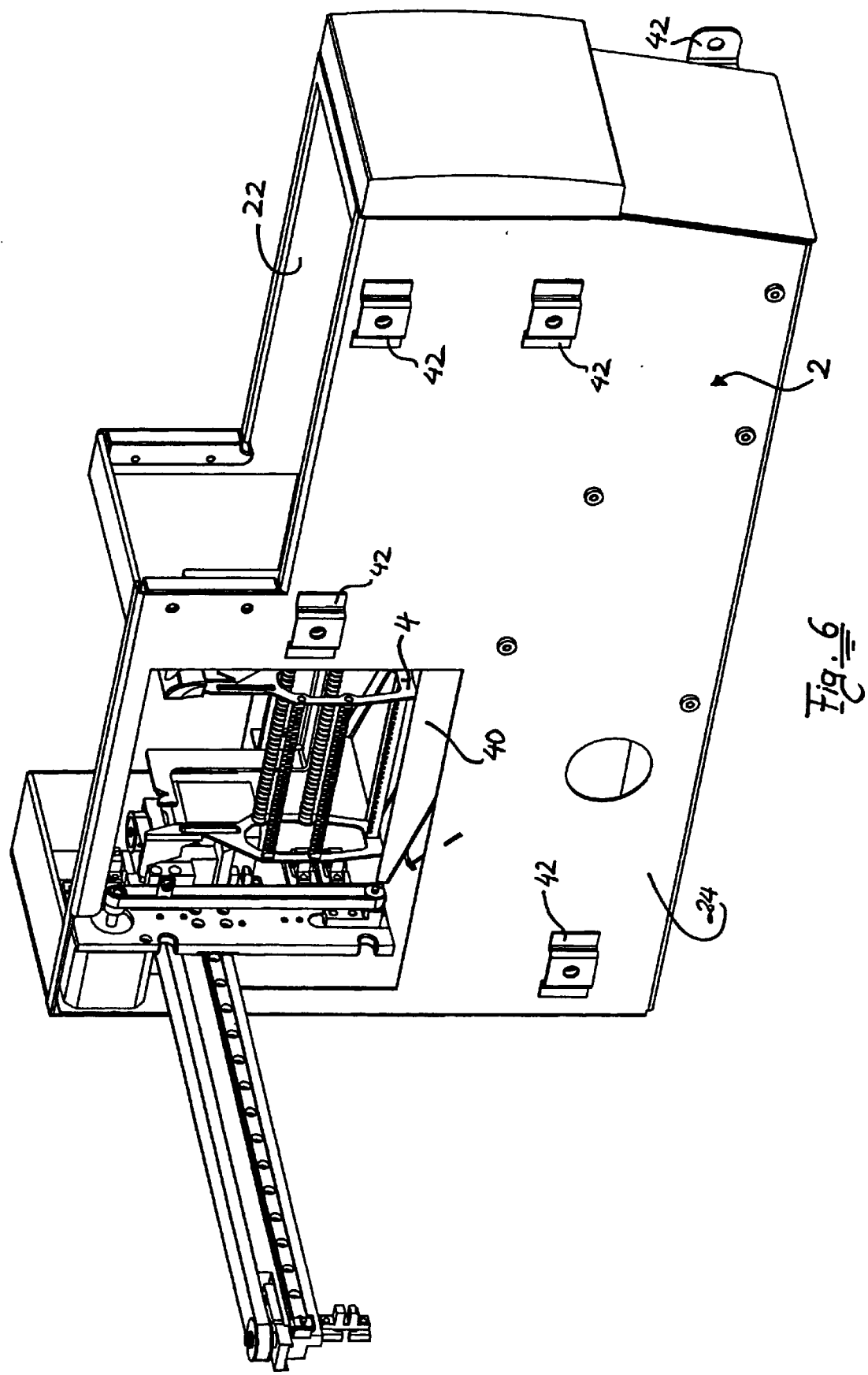
FIG. 6 is a perspective depiction of the loading station with the empty rack temporarily stored in the loading station.

FIG. 6 depicts the situation in which the empty rack 4 is deposited in the interior of unit 2. Provided between first and second side walls 22 and 24 in the interior of unit 2 is a storage position 40 that, in this embodiment, is configured as a chute. Once the empty rack 4 has reached the interior of unit 2 by way of transport apparatus 9, gripper 12 is lowered and rack 4 is snapped out. Rack 4 is located in storage position 40, which is configured as a chute (inclined plane). The empty rack 4 slides on the chute toward front panel 25. Unit 2 is once again ready to accept a new rack 4 with specimen slides 6. The embodiment selected, with the chute as storage position 40 alongside transfer position 8, allows a very narrow configuration for unit 2, which in turn results in optimum utilization of work surfaces in a laboratory. Several attachment elements 42, which coact with corresponding attachment elements on the upstream stainer 1 or downstream coverslipper 3, are provided on side walls 22 and 24.

Figure 7:
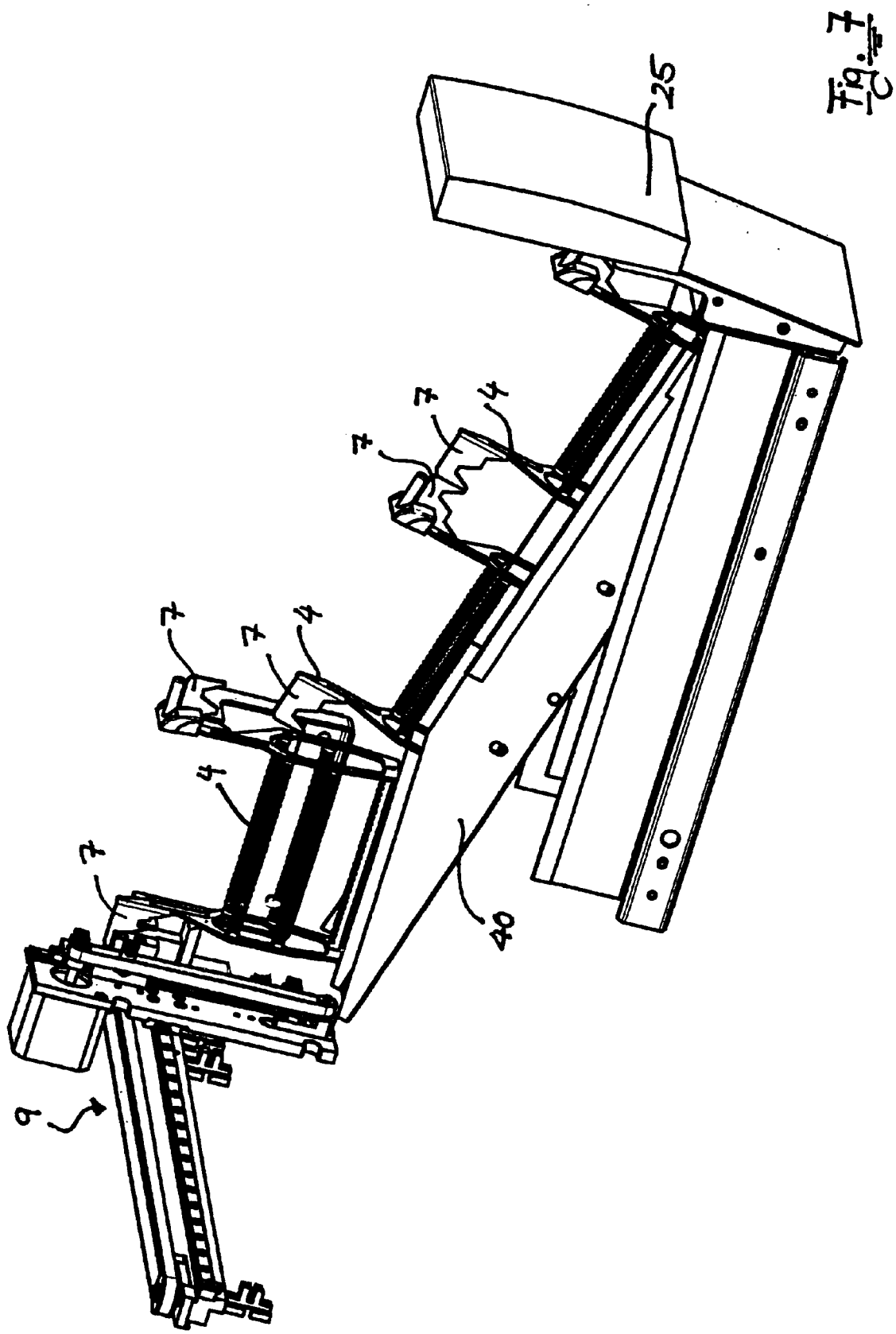
FIG. 7 is a perspective depiction of the elements in the interior of the loading station, with two empty racks temporarily stored in the loading station and one rack in the transfer position.

FIG. 7 shows a view into the interior of unit 2, the housing having been omitted to achieve better clarity. Two empty racks 4 have already been deposited in storage position 4. As already described above, racks 4 slide on the chute toward front panel 25. If more than one rack 4 is present in the storage position, the first rack rests against front panel 25 of unit 2 and the next rack 4 is braced with angled piece 7 against angled piece 7 of the first rack 4. Passage 20 is open, and the transport apparatus can pick up a rack 4 with specimen slides 6 from stainer 1.

The invention has been described with reference to a particular exemplary embodiment. It is nevertheless self-evident that changes and modifications can be made without thereby leaving the range of protection of the claims below.

PARTS LIST

1 Stainer
1a Side wall

2 Unit
3 Coverslipper
4 Rack
5 Groove
6 Specimen slides
7 Angled piece
8 Transfer position
9 Transport apparatus
10 Opening
11 Rail
12 Gripper
12a Belt
12b Support element
14 First motor
16 Baseplate
17 Light barriers
18 Second motor
19 Belt
20 Passage
21 First cutout
22 First side wall
23 Second cutout
24 Second side wall
25 Front panel
27 Housing
28 Bottom
29 Back wall
30 Opening
31 Side wall
40 Storage position
42 Attachment elements

What is claimed is:

1. A unit (2) for automatic delivery of specimen slides (6) to a coverslipper (3), the unit (2) comprising:

a housing (27) including a bottom, a front panel (25), a back wall (29) opposite the front panel (25), and a first and a second side wall (22 and 24) opposite one another, the housing (27) having a passage (20) therethrough defined substantially by a first and a second cutout (21 and 23) in the first and the second side walls (22 and 24);

a transfer position (8) for a rack (4) of specimen slides (6) provided near the first cutout (21) in the first side wall (22); and a transport apparatus (9) extending out from the transfer position (8) to beyond the second cutout (23) in the second side wall (24).

2. The unit as defined in claim 1, wherein the transport apparatus (9) is substantially parallel to the back wall (29) of the unit (2).

3. The unit as defined in claim 1, wherein the transport apparatus (9) comprises a rail (11) parallel to the back wall (29) of the unit (2), and a gripper (12) for a rack (4) displaceable on the rail (11) perpendicular to and parallel to the rail (11).

4. The unit as defined in claim 3, wherein the gripper (12) is connected to a belt (12a) that is driven via a first motor (14); and the gripper (12), the belt (12a), and the first motor (14) are carried by a baseplate (16), the baseplate (16) being movable along the rail (11) by way of a belt (19) driven by a second motor (18).

5. The unit as defined in claim 1, wherein a storage position (40) for racks (4) without specimen slides (6) is provided between the first and the second side walls (22 and 24).

6. The unit as defined in claim 5, wherein the storage position is defined by a chute that is arranged at an inclination with respect to the bottom in such a way that the racks without specimen slides slide toward the front panel.

7. The unit as defined in claims 6, wherein the front panel opens to allow the racks without specimen slides to be removed through the opened front panel.

8. The unit as defined in claim 1, wherein at least one attachment element (42), with which the unit (2) can be connected to upstream and downstream stations, is provided respectively on the first and second side walls that are opposite one another.

9. A method for automatic delivery of specimen slides to a coverslipper (3), the method comprising the steps of:

A) depositing a rack (4) with specimen slides (6) in a transfer position (8) of a unit (2) for delivering specimen slides to the coverslipper (3);

B) picking up the rack (4) from the transfer position (8) using a transport apparatus (9);

C) displacing the rack (4) in the unit (2) toward the coverslipper (3); and

D) lowering the rack (4) with the specimen slides (6) into the coverslipper (3).

10. The method as defined in claim 9, wherein a stainer (1) upstream from the unit (2) queries the coverslipper (3) as to whether a deposit position for a rack (4) with specimen slides (6) is open in the coverslipper (3).

11. The method as defined in claim 10, wherein the querying of the coverslipper (3) is repeated at periodic intervals if the deposit position is not open.

12. The method as defined in claim 9, comprising the further steps of:

E) detecting the rack (4) with specimen slides that has been deposited in the coverslipper (3), and initiating the coverslipping operation;

F) removing of the emptied rack (4) from the coverslipper (3) by means of the transport device (9); and G) depositing of the empty rack (4) in a storage position (40) provided in the unit (2).

13. The method as defined in claim 12, wherein the storage position (40) is defined by a chute that is arranged at an inclination with respect to horizontal in such a way that the racks (4) without specimen slides slide toward a front panel (25) of the unit (2).

* * * * *